US009095631B2

(12) United States Patent  
Colabufo et al.

(10) Patent No.: US 9,095,631 B2  
(45) Date of Patent: Aug. 4, 2015

(54) TETRAHYDROISOQUINOLINE COMPOUNDS FOR USE IN THE DIAGNOSIS AND TREATMENT OF NEURODEGENERATIVE DISEASES

(75) Inventors: Nicola Antonio Colabufo, Bari (IT); Francesco Berardi, Bari (IT); Mariangela Cantore, Bari (IT); Marialessandra Contino, Bari (IT); Marcello Leopoldo, Bari (IT); Roberto Perrone, Bari (IT)

(73) Assignee: UNIVERSITA DEGLI STUDI DI BARI "ALDO MORO", Bari (IT)

( * ) Notice: Subject to any disclaimer, the term of this patent is extended or adjusted under 35 U.S.C. 154(b) by 0 days.

(21) Appl. No.: 14/119,539

(22) PCT Filed: May 24, 2011

(86) PCT No.: PCT/EP2011/058469  
§ 371 (c)(1),  
(2), (4) Date: Nov. 22, 2013

(87) PCT Pub. No.: WO2012/159666  
PCT Pub. Date: Nov. 29, 2012

(65) Prior Publication Data  
US 2014/0112868 A1 Apr. 24, 2014

(51) Int. Cl.
| | |
|---|---|
| A61K 51/00 | (2006.01) |
| A61M 36/14 | (2006.01) |
| A61K 51/04 | (2006.01) |
| C07D 413/04 | (2006.01) |
| C07D 417/04 | (2006.01) |
| C07B 59/00 | (2006.01) |
| C07D 413/06 | (2006.01) |
| C07D 417/06 | (2006.01) |

(52) U.S. Cl.  
CPC ............ *A61K 51/0455* (2013.01); *C07B 59/002* (2013.01); *C07D 413/04* (2013.01); *C07D 413/06* (2013.01); *C07D 417/04* (2013.01); *C07D 417/06* (2013.01)

(58) Field of Classification Search  
USPC ........................................................ 424/1.85  
See application file for complete search history.

(56) References Cited

U.S. PATENT DOCUMENTS

| 6,562,836 B1 | 5/2003 | Szarek et al. |
|---|---|---|
| 2004/0248876 A1 | 12/2004 | Szarek et al. |
| 2008/0227767 A1 | 9/2008 | Szarek et al. |
| 2009/0274624 A1* | 11/2009 | Pike et al. .................... 424/1.89 |

FOREIGN PATENT DOCUMENTS

WO      00/71101      11/2000

OTHER PUBLICATIONS

Colabufo et al. Bioorg. Med. Chem. 16 (2008) 3732-3743.*  
Colabufo et al. ChemMedChem 2009, 4, 188-195.*  
Int'l Search Report for PCT/EP2011/058469, three pages, mailed Sep. 28, 2011.  
Written Opinion for PCT/EP2011/058469, five pages, mailed Sep. 28, 2011.

* cited by examiner

*Primary Examiner* — Michael G Hartley  
*Assistant Examiner* — Sean R Donohue  
(74) *Attorney, Agent, or Firm* — Nixon & Vanderhye PC

(57) ABSTRACT

The invention relates to a new class of compounds with high affinity and selectivity towards P-glycoprotein. The invention also relates to the utilization of such compounds in the in vivo diagnosis of neurodegenerative diseases and as medicaments for use in the prevention and treatment of neurodegenerative disease involving P-glycoprotein.

20 Claims, No Drawings

TETRAHYDROISOQUINOLINE COMPOUNDS FOR USE IN THE DIAGNOSIS AND TREATMENT OF NEURODEGENERATIVE DISEASES

This application is the U.S. national phase of International Application No. PCT/EP2011/058469, filed 24 May 2011; the entire contents of which is hereby incorporated by reference.

TECHNICAL FIELD OF THE INVENTION

The invention relates to a new class of compounds with high affinity and selectivity towards P-glycoprotein. The invention also relates to the utilization of such compounds in the in vivo diagnosis of neurodegenerative diseases and as medicaments for use in the prevention and treatment of neurodegenerative diseases involving P-glycoprotein.

BACKGROUND OF THE INVENTION

P-gp (P-glycoprotein) is a membrane transporter belonging to the ABC (ATP Binding Cassette) family and is expressed in several organs such as kidney, liver, lung, intestine and central nervous system (CNS). This protein is involved in active transport of xenobiotics and therefore plays a key role in absorption and detoxification processes. P-gp is encoded by MDR1 and MDR2 genes in humans.

Recently, a correlation between the alteration of P-gp activity and/or expression in the CNS and the onset of neurodegenerative diseases such as Parkinson's and Alzheimer's has been demonstrated (Vogelgesang, S. et al. 2002, *Pharmacogenetics*, 12, 535-541; Rapposelli et al., 2009, *Curr. Top. Med. Chem.*, 9, 209-217).

In particular, Alzheimer's disease is characterized by the presence of plaques of insoluble β-amyloid (Aβ) and neurofibrillary tangles. Recently, in the brain of AD patients an inverse correlation between Aβ accumulation in CNS and P-gp activity has been detected (Kuhnke, D. et al., 2007, *Brain pathol.*, 17, 347-353). This finding led to assign to P-gp a critical role in Aβ efflux from the brain.

Therefore, P-gp is important not only as a target for the prevention and treatment of the neurodegenerative disorders, but also for the development of radiotracers for use in imaging method such as PET and SPECT analyses to detect the activity of this protein, and therefore the onset of neurodegenerative disease.

In the last years, some radiotracers were developed, even if their diagnostic use was limited by their low basal uptake, the production of radio metabolites falsifying the analysis and their poor selectivity towards other ABC transporters.

P-gp substrates such as [$^{11}$C] verapamil, [$^{11}$C] loperamide and [$^{11}$C]N-desmethyl-loperamide were used to visualize the activity of P-gp, but they showed a low basal uptake at the blood brain barrier (BBB) and the production of radio metabolites alternating the analysis. (Bart, J. et al., 2003, *Neuroimage*, 20, 1775-1782, Liow, J. S. et al., 2009, *J. Med. Chem.*, 49, 1328-1335).

P-gp inhibitors such as [$^{11}$C] elacridar, [$^{11}$C] laniquidar and [$^{11}$C] tariquidar were tested for the detection of P-gp expression. (Dörner, B. et al. 2009, *J. Med. Chem*, 52, 6073-6082, Luurtsema, G. et al., 2009, *Nucl. Med. Biol.*, 36, 6073-6082; Bankstahl, J. P. et al., 2008, *J. Nucl. Med. Chem.*, 49, 1328-1335) but the absence of selectivity towards other ABC transporters, such as BCRP, the low brain uptake and a different dose-dependent behavior has limited their diagnostic use.

In Kannan et al. (Kannan, P. et al., 2009, *Clin. Pharmacol. Ther.*, 86, 368-377 and Kannan, P. et al., 2010, *ACS Chem. Neurosci*) the pharmacokinetic and pharmacodynamic limits in the development of P-gp PET tracer are shown.

Other compounds for use in the in vivo diagnosis of Alzheimer disease are shown in the following international patent WO0071101.

Scope of the present invention is to provide novel compounds for use as radiotracers in vivo diagnosis of neurodegenerative diseases involving P-glycoprotein activity without the disadvantages of prior art's compounds.

SUMMARY OF THE INVENTION

The present invention is based on the identification of a novel family of compounds able to interfere with P-gp activity as inhibitors or as modulators thereof, but with poor or no activity towards the Multidrug Resistance associated Protein (MRP1), another transporter belonging to the ABC superfamily.

The compounds developed by the inventors present different points of radiolabelling. This property together with the properties described above makes such compounds high specific radiotracers useful for in vivo diagnosis of neurodegenerative diseases involving P-gp activity.

Moreover the pharmacological activity of these compounds is highly advantageous in terms of new therapeutic approach to neurodegenerative diseases involving P-gp activity. Indeed, P-gp inducers should be employed in neurodegenerative diseases to clean CNS areas from beta amyloid plaques.

Hence, object of the present invention is a family of compounds having the general formula as indicated in claim 1.

A second object of the invention are compounds selected from the above-indicated family isotopically radio labeled for use in vivo diagnosis of a neurodegenerative disease involving P-gp activity.

A third object of the invention are compounds selected from the above-indicated family for use as medicaments, in particular as inhibitor or as modulator of the P-glycoprotein function in the prevention or treatment of pathologies involving P-glycoprotein, in particular wherein said pathology is Alzheimer's or Parkinson's disease.

A fourth object of the invention is a diagnostic imaging composition comprising as imaging agent a compound selected from the above-indicated family isotopically radio labeled and a carrier.

A fifth object of the invention is a pharmaceutical composition comprising the compounds selected from the above-indicated family and a pharmacologically acceptable excipient and/or diluent.

A further object of the invention is a pharmaceutical kit formed by a first element containing a compound selected from the above-indicated family and a second element containing radionuclide suitable for imaging.

A further object of the invention is a method of preparing the compounds selected from the above-indicated family.

Other objects will be made evident in the light of the following detailed description.

DETAILED DESCRIPTION OF THE INVENTION

Compounds of the Invention

The invention relates to a family of novel compounds having the following general formula:

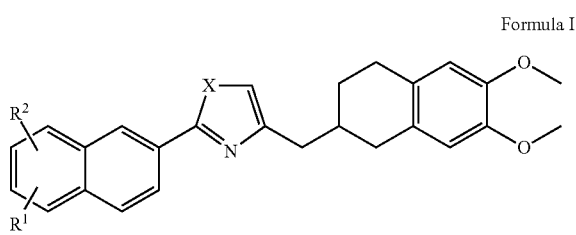

Formula I wherein:

X is oxygen or sulfur;

$R^1$ and $R^2$ may be respectively on position 5, 6, 7 or 8 of the naphthalene core and are selected independently of each other from: H, OH, $OCH_3$, $NH_2$, $NO_2$ or a halogen atom selected from: F, Cl, Br, I or an alkyl group selected from: methyl, ethyl, n-propyl, iso-propyl, n-butyl, iso-butyl or ter-butyl.

Preferred subgroups are those wherein $R^2$ is H.

A specific subgroup of the general formula indicated above comprises molecules wherein X is oxygen, $R^2$ is H and $R^1$ is H, F, Br, $OCH_3$ or OH.

A second specific subgroup comprises molecules wherein X is sulfur $R^2$ is H and $R^1$ is H, F, Br, $OCH_3$ or OH.

Specific examples of compounds of the invention are: 1,2,3,4-tetrahydro-6,7-dimethoxy-2-((2-(naphthalen-6-yl)ox-azol-4-yl)methyl)isoquinoline, (2-((2-(2-Bromonaftalen-6-il)thiazol-4-il)metil)-1,2,3,4-tetraidro-6,7-dimetossiisochinolina, 2-((2-(2-fluoronaphthalen-6-yl)oxazol-4-yl)methyl)-1,2,3,4-tetrahydro-6,7-dimethoxyisoquinoline, 2-((2-(2-hydroxynaphthalen-6-yl)oxazol-4-yl)methyl)-1,2,3,4-tetrahydro-6,7-dimethoxyisoquinoline, 1,2,3,4-tetrahydro-6,7-dimethoxy-2-((2-(2 methoxynaphthalen-6-yl)thiazol-4-yl)methyl)isoquinoline.

Synthesis Process

The compounds of general formula I were produced as reported in Scheme I by reacting the appropriately substituted derivative of naphthalene (II) with the 1,3-dichloroacetone (C) and then reacting the product (III) with the 6,7-dimethoxy-1,2,3,4-tetrahydroisoquinoline (IV).

Scheme I

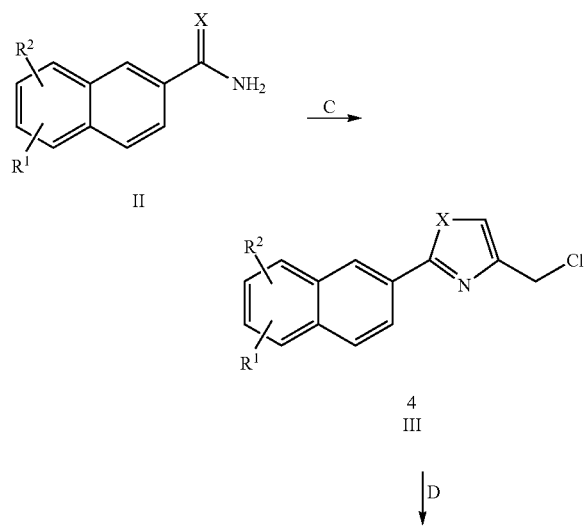

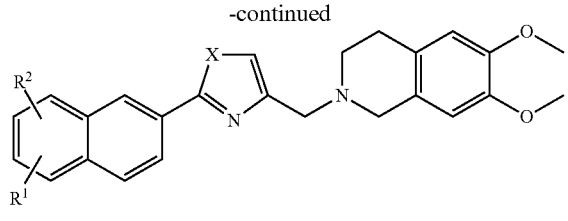

IV

Radio Labelled Compounds

The compounds selected from the above-indicated family may be radiolabelling for use in vivo diagnosis of a neurodegenerative disease involving P-glycoprotein function.

All the radio isotopes and methods known in the art, suitable for labelling the compounds of the invention, may be used. For example isotopes such as $^3H$, $^{11}C$, $^{14}C$, $^{13}N$, $^{15}O$, $^{18}F$ $^{19}F$, $^{75}Br$, $^{76}Br$, $^{79}Br$, $^{123}I$, $^{124}I$, $^{127}I$, $^{131}I$ or $^{34m}Cl$ may be used.

The compounds may be advantageously radio labeled in the last synthetic step. This is advantageous because radio synthesis will be done in nuclear medicine centers where the radioligand will be injected for in vivo evaluation. Radiolabelling in the last step is also advantageous for the short decay time of radioisotopes (for example 2 h for $^{18}F$ and 20 minutes for $^{11}C$).

Pharmaceutical Compositions

A further object of the invention is a pharmaceutical composition comprising the compounds selected from the above-indicated family and a pharmacologically acceptable excipient and/or diluent. Preferably these compositions are in unit dosage forms such as tablets, pills, capsules, powders, granules, sterile parenteral solutions or suspensions, metered aerosol or liquid sprays, drops, ampoules, auto-injector devices or suppositories; for oral, parenteral, intranasal, sublingual or rectal administration, or for administration by inhalation or insufflation. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dose of the type described above containing from 0.1 to about 500 mg of the active ingredient of the present invention. Typical unit dose contain from 1 to 50 mg, of the active ingredient. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, acetyl alcohol and cellulose acetate.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinyl-pyrrolidone or gelatin. Thus, based on the above, a variety of pharmaceutically acceptable doses are provided.

Also, it is noted that the term "pharmaceutically acceptable salt(s)" refers to salts derived from treating a compound of formula I with an organic or inorganic acid such as, for example, acetic, lactic, citric, cinnamic, tartaric, succinic, fumaric, maleic, malonic, mandelic, malic, oxalic, propionic, hydrochloric, hydrobromic, phosphoric, nitric, sulfuric, glycolic, pyruvic, methanesulfonic, ethanesulfonic, toluenesulfonic, salicylic, benzoic, or similar.

Compositions comprising compounds of Formula I and a pharmaceutical acceptable carrier or diluent may advantageously be used in the treatment of pathologies involving P-glycoprotein, in particular pathologies such as Alzheimer's and Parkinson's disease.

Unless otherwise specified, when referring, to the compounds of formula I per se, to any pharmaceutical composition thereof, the present invention includes all of the salts, hydrates, solvates, complexes, and prodrugs of the compounds of the invention. Prodrugs are any covalently bonded compounds, which releases the active parent pharmaceutical according to formula I.

Imaging Composition

A further object of the invention is a diagnostic imaging composition comprising as imaging agent the compounds selected from the above-indicated families isotopically radio labeled and a carrier. In accordance with the invention, the radio labelled compounds according to Formula I may be administered in a single unit injectable dose. Any of the common carriers known to those with skill in the art, such as sterile saline solution or plasma, can be utilized after radio labelling for preparing the injectable solution to diagnostically imaging in accordance with the invention. Such techniques include the step of bringing into association the active ingredient and the pharmaceutical carrier(s) or diluent(s). In general the formulations are prepared by uniformly and intimately bringing into association the active ingredient with the liquid carrier.

Generally, the unit dosage to be administered for a diagnostic agent has a radioactivity of about 10 MBq to about 15 MBq. The solution to be injected at unit dose is from about 4 mg/mL to about 7.5 mg/ml. For diagnostic purposes after intravenous administration, imaging of the organ in vivo can take place in a matter of a few minutes. However, imaging takes place, if desired, in hours or even longer, after injecting into patients. In most instances, a sufficient amount of the administered dose will accumulate in the area to be imaged for example within about 1 hour to permit the taking of diagnostic images. Any conventional method of imaging for diagnostic purposes can be utilized in accordance with this invention as positron emission tomography (PET) or Single photon emission computed tomography (SPECT).

The diagnostic imaging compositions of the invention are useful for use in vivo diagnosis of a neurodegenerative disease involving P-gp activity such as Alzheimer's or Parkinson's disease.

Kit

The pharmaceutical kit of the present invention is formed by a first element containing a compound of the family described above and a second element containing radionuclide suitable for imaging.

The kit will allow user to obtain compound of Formula I ready to use for imaging.

Method for In Vivo Diagnosis

It is a further object of the invention a method for diagnosis of neurodegenerative disease involving P-gp activity comprising:

administering to a mammal, preferably a human, an effective amount of a isotopically radio labelled compound of the family described above;

imaging the in vivo P-gp.

The imaging technique may be for example Positron emission tomography (PET) or Single positron emission computerized tomography (SPECT).

In the method of in vivo diagnosis the effective amount administered of the isotopically labelled compounds of the present invention will depend on the particular condition to be diagnosed, the age, weight and the overall physical condition of the particular patient as it is well known to the experts in the field.

Method for Treatment

It is a further object of the invention a method for treating of a neurodegenerative disease by modulating P-glycoprotein activity, comprising administering to a patient an effective amount of a compound of the families described above. In particular, the Alzheimer's or Parkinson's disease.

In the method of treatment the effective amount administered and frequency of administration of the compounds of the present invention will depend on the particular condition to be treated, the severity of the condition, age, weight and the overall physical condition of the particular patient as well as on other medicaments the patient is taking, as it is well known to the experts in the field.

Effective dosages that can be administered are from 2 mg/Kg to 10 mg/Kg body weight.

EXAMPLES AND BIOLOGICAL EXPERIMENTATION

The invention is detailed hereinafter via the following examples of preparation and through the following biological testing. By the methods described above the following intermediates and final compounds have been obtained.

Example 1

Synthesis Process According to the Following Scheme

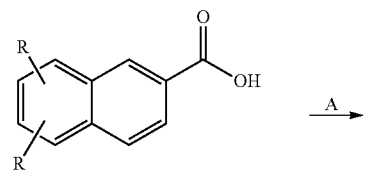

1

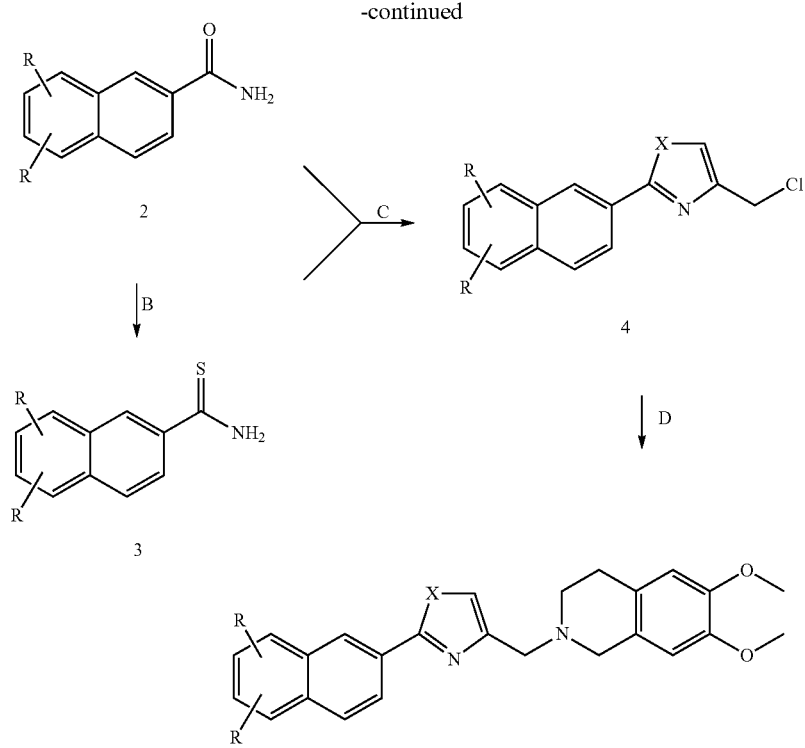

R = H, Halogens, Alkyl, O-Alkyl, NH₂, NO₂, OH  X = O, S.

Reagents: SOCl₂, Et₃N (A); NH₄OH, CH₂Cl₂ (B); Lawesson's Reagent, THF (C); ClCH₂COCH₂Cl, (D); Na₂CO₃, DMF, 6,7-dimethoxy-1,2,3,4-tetrahydroisoquinoline(E).

Procedure for the Synthesis of Amides 2

Amides 2 were prepared by reaction of naphtoic acids 1 (1 mmol) commercially available with 2 mL of SOCl₂ and 0.5 mL of Et₃N. The mixture was refluxed for 30 minutes and acyl chloride was dissolved in CH₂Cl₂ and was added to a solution of NH4OH. The mixture was shaken at room temperature for 4-24 h. The alkaline layer was extracted with CH₂Cl₂ and organic layers were combined and dried over Na₂SO₄ and concentrated. In some cases, the amide precipitated before separation of the two layers and was isolated by filtration. The amides were purified by column chromatography in the elution conditions reported in the experimental data for each example reported.

Procedure for the Synthesis of Tioamides 3

Naphthylamide 2 (2 mmol) and Lawesson's Reagent (2.2 mmol) was refluxed in THF dry (25 mL) for 3-12 h. The mixture was cooled and H₂O was added, the aqueous layer was extracted with CH₂Cl₂ (25 mL×3). The organic layers were combined, dried on Na₂SO₄ and evaporated. Tioamides were purified by column chromatography in the experimental conditions following reported.

Procedure for the Synthesis of Chlorides 4

A mixture of amide 2 (1 mmol) and 1,3-dichloroacetone (1.2 mmol) was warmed at T=200° C. in homogeneous for 4-10 h. In case of tioamides 3 the mixture was dissolved in EtOH (50 mL) with the same stoichiometric values. Aqueous layer was extracted with CH₂Cl₂ (25 mL×3). The organic layers were combined and dried on Na₂SO₄. Ossazoles and thiazoles derivatives were purified by column chromatography in the experimental conditions reported for each compound.

Procedure for the Synthesis of Compounds 5

A solution of chloro intermediate 4 (1 mmol), 6,7-dimethoxy-1,2,3,4-tethraydroisoquinoline (2 mmol), Na₂CO₃ (2 mmol) in DMF was refluxed overnight. DMF was removed in vacuo and H₂O was added. The layer was extracted with CH₂Cl₂ (25 mL×3). Organic layers were dried on Na₂SO₄ and the solvent was removed under pressure. Compounds were purified by chromatography in the eluition condition reported below. All amines were salified by HCl (g) and recrystallized by Et₂O.

Example 2

End Compounds IV Preparation Some Example of Amides 2

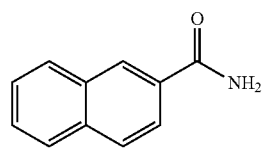 [SMILES: NC(=O)c1ccc2ccccc2c1]

2-Naphthamide

Formula: $C_{11}H_9NO$
Physical State: white solid.

Yield: 87%.
Pf: 195-197° C.
GC-MS m/z: 171 (M+, 86), 155 (100), 127 (97).

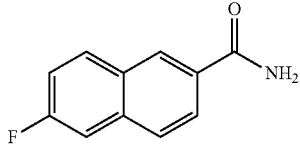 [SMILES: NC(=O)c1ccc2cc(F)ccc2c1]

6-Fluoronaphthalene-2-carboxamide

Formula: $C_{11}H_8NOF$
Physical State: white solid.
Yield: quantitative.
Pf: 211-214° C. dec.
$^1$H-NMR (δ): 6.05 (s broad, 2H, NH$_2$), 7.30-8.35 (m, 6H, aromatic).
GC-MS m/z: 189 (M+, 77), 173 (100), 145 (86).

6-hydroxynaphthalene-2-carboxamide

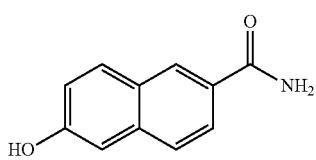 [SMILES: NC(=O)c1ccc2cc(O)ccc2c1]

Formula: $C_{11}H_9NO_2$
Physical State: yellow solid.
Yield: 28%.
Chromatography: CHCl$_3$/AcOEt 7:3
Pf: 186-190° C.
$^1$H-NMR δ: 6.63 (s broad, NH$_2$), 7.03-8.35 (m, 6H, aromatic), 9.52 (s broad, OH).
GC-MS m/z: 187 (M+, 86), 171 (100), 143 (45).

Some Example of Tioamides 3

6-Bromonaphthalene-2-carbothioamide

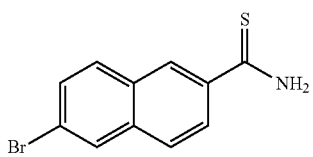 [SMILES: NC(=S)c1ccc2cc(Br)ccc2c1]

Formula: $C_{11}H_8NSBr$
Physical State: yellow solid.
Yield: quantitative.
Cromatography: CHCl$_3$/AcOEt 8:2
GC-MS: m/z: 265 (M+, 95), 267 (M+2, 100), 232 (77).

6-Methoxynaphthalene-2-carbothioamide

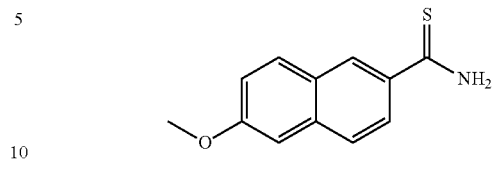

Formula: $C_{12}H_{11}NOS$
Physical State: yellow solid.
Yield: 57%.
Cromatography: CH$_2$Cl$_2$/AcOEt 9:1
$^1$H-NMR . . . δ: 3.94 (s, 3H, OCH$_3$), 7.13-8.34 (m, 6H, aromatic), 7.45 (s broad, 2H, NH$_2$). ESI$^+$/MS m/z: 218 [M+H]$^+$. ESI$^+$/MS/MS m/z: 201 (100), 159 (39).

Some Examples of Oxazoles 4

4-(Chloromethyl)-2-(naphthalen-6-yl)oxazole

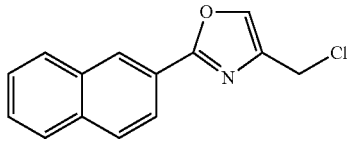 [SMILES: ClCc1coc(-c2ccc3ccccc3c2)n1]

Formula: $C_{14}H_{10}NOCl$
Physical State: yellow solid
Yield: 77%.
Cromatography: petroleum ether/AcOEt 8:2.
GC-MS m/z: 243 (M+, 32), 245 (M+2, 9), 139 (100).
ESI$^+$/MS m/z: 400 [M+H]$^+$. ESI$^+$/MS/MS m/z: 208 (56), 153 (100).

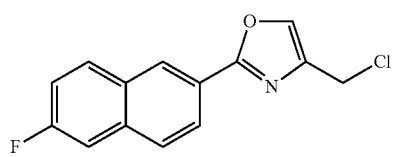 [SMILES: Fc1ccc2cc(-c3nc(CCl)co3)ccc2c1]

4-(Chloromethyl)-2-(2-fluoronaphthalen-6-yl)oxazole

Formula: $C_{14}H_{10}NOFCl$
Physical State: white solid
Yield: 54%.
Cromatography: petroleum ether/AcOEt 9:1.
Pf: 109-111° C.
$^1$H-NMR δ: 4.62 (s, 2H, CH$_2$), 7.28-8.54 (m, 7H, aromatic).
GC-MS m/z: 261 (M+, 50), 263 (M+2, 18), 171 (100).

4-(Chloromethyl)-2-(2-hydroxynaphthalen-6-yl)oxazole

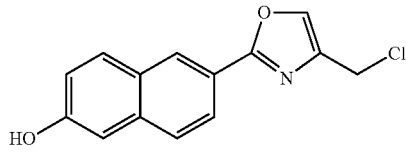 [SMILES: Oc1ccc2cc(-c3nc(CCl)co3)ccc2c1]

Formula: $C_{13}H_{10}NO_2Cl$
Physical State: white solid
Yield: 47%.
Cromatography: $CHCl_3$
$^1$H-NMR δ: 4.53 (s, 2H, $CH_2$), 7.06-8.33 (m, 7H, aromatic), 9.30 (s broad, OH).
GC-MS m/z: 259 (M+, 72), 261 (M+2, 23), 169 (100).

Some Example of Thiazoles 4

2-(2-Bromonaphthalen-6-yl)-4-(chloromethyl)thiazole

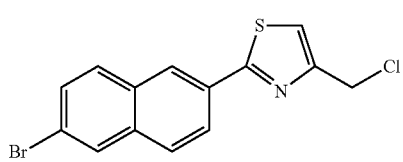 [SMILES: ClCc1csc(-c2ccc3cc(Br)ccc3c2)n1]

Formula: $C_{14}H_9NSBrCl$
Physical State: white solid
Yield: 61%.
Cromatography: $CH_2Cl_2$
Pf: 103-105° C.
$^1$H-NMR δ: 4.80 (s, 2H, $CH_2$), 7.36-8.40 (m, 7H, aromatic).
GC-MS m/z: 339 (M+, 100), 341 (M+2, 27), 304 (45).

4-(Chloromethyl)-2-(2-methoxynaphthalen-6-yl)thiazole

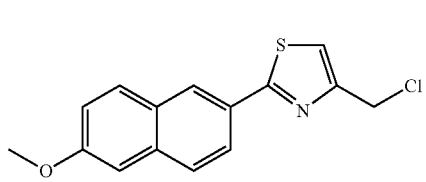 [SMILES: COc1ccc2cc(-c3nc(CCl)cs3)ccc2c1]

Formula: $C_{15}H_{12}NOSCl$
Physical State: white solid
Yield: 89%.
Cromatography: $CHCl_3$
ESI$^+$/MS m/z: 290 [M+H]$^+$. ESI$^+$/MS/MS m/z: 254 (100), 256 (6).

Some Examples of Amines 5

1,2,3,4-tetrahydro-6,7-dimethoxy-2-((2-(naphthalen-6-yl)oxazol-4-yl)methyl)isoquinoline

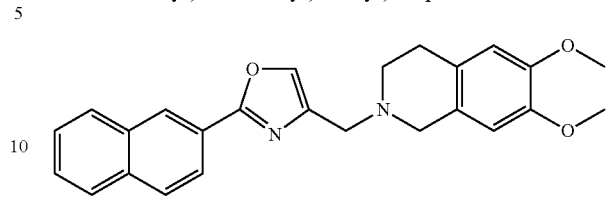

Formula: $C_{25}H_{24}N_2O_3$
Physical State: red solid
Yield: 64%.
Cromatography: $CHCl_3$
Pf: 232-235° C.
$^1$H-NMR (δ): 2.94 (s, 4H, $CH_2NCH_2$), 3.75-3.79 (d, 4H, $NCH_2CH_2$), 3.82-3.88 (m, 6H, 2 di $OCH_3$), 6.52-8.57 (m, 10H, aromatic).
ESI$^+$/MS m/z: 400 [M+H]$^+$. ESI$^+$/MS/MS m/z: 208 (56), 153 (100).

(2-((2-(2-Bromonaftalen-6-il)thiazol-4-il)metil)-1,2,3,4-tetraidro-6,7-dimetossiisochinolina

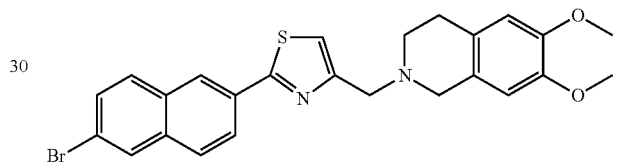

Formula: $C_{25}H_{23}N_2O_2SBr$
Physical State: olio scuro
Resa: 30%.
Cromatografia: ($CH_2Cl_2$)
Pf: 221-224° C.
$^1$H-NMR (δ: 2.88 (s, 4H, $CH_2NCH_2$), 3.72-3.96 (d, 4H, $NCH_2CH_2$), 3.82-3.884 (s, 6H, 2 di $OCH_3$), 6.51-8.42 (m, 9H, aromatici).
ESI$^+$/MS m/z: 497 [M+H]$^+$. ESI$^+$/MS/MS m/z: 304 (84), 192 (100).

2-((2-(2-fluoronaphthalen-6-yl)oxazol-4-yl)methyl)-1,2,3,4-tetrahydro-6,7-dimethoxyisoquinoline

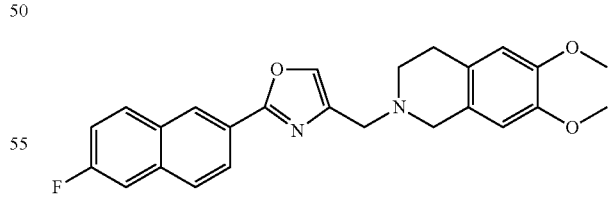

Formula: $C_{25}H_{23}N_2O_3F$
Physical State: white solid
Yield: 56%
Cromatography: $CH_2Cl_2$/MeOH 98:2
Pf: 231-234° C.
$^1$H-NMR δ: 2.87 (s, 4H, $CH_2NCH_2$), 3.70-3.75 (d, 4H, $NCH_2CH_2$), 3.81-3.84 (m, 6H, 2 di $OCH_3$), 6.51-8.56 (m, 9H, aromatic).
GC-MS m/z: 418 (M+, 0.86), 192 (100), 171 (18).

2-((2-(2-hydroxynaphthalen-6-yl)oxazol-4-yl)methyl)-1,2,3,4-tetrahydro-6,7-dimethoxyisoquinoline

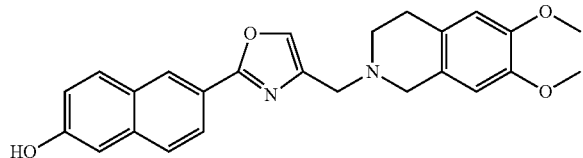 [SMILES: COc1cc2c(cc1OC)CN(Cc1coc(-c3ccc4cc(O)ccc4c3)n1)CC2]

Formula: $C_{25}H_{24}N_2O_4$
Physical State: yellow oil.
Cromatography: $CH_2Cl_2$/MeOH 99:1
Pf: 249-252° C. dec.
ESI$^+$/MS m/z: 417 [M+H]$^+$. ESI$^+$/MS/MS m/z: 224 (97), 169 (100).

1,2,3,4-tetrahydro-6,7-dimethoxy-2-((2-(2-methoxynaphthalen-6-yl)thiazol-4-yl)methyl)isoquinoline

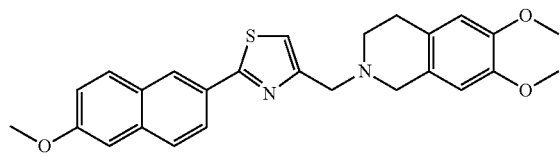

Formula: $C_{26}H_{26}N_2O_3S$
Physical State: yellow solid
Resa: 55%.
Cromatography: $CHCl_3$
Pf: >250° C. dec.
$^1$H-NMR δ: 2.88 (s, 4H$H_2NCH_2$), 3.75-3.95 (d, 4H, $NCH_2CH_2$), 3.81-3.93 (m, 9H, 3 di $OCH_3$), 6.52-8.37 (m, 9H, aromatic).
ESI$^+$/MS m/z: 447 [M+H]$^+$.

Procedure for $^{11}$C Radiosynthesis.

[$^{11}$C]-Methyl iodide is trapped in a solution of desmethyl derivative (for example 0.5 mg in 0.5 mL anhydrous DMSO). Shortly before the arrival of [$^{11}$C]-methyl iodide, 7 μL of NaOH (5 M) was added to the precursor solution. The reaction was heated for 4 min at 80° C. After addition of $H_2O$ (2 mL) $^{11}$C-radiolabelled compound was purified on reverse phase chromatography column with 100 mM $NaH_2PO_4$: EtOH 1:1 (v/v) as mobile phase. The quality control of the product is then carried out on preparative HPLC before use in vivo.

Procedure for 18F Radiosynthesis

Precursor for $^{18}$F radiosynthesis was 6-tosylethoxy-7-methoxy-1,2,3,4-tetrahydroisoquinoline derivative that was prepared starting from 6-hydroxy-7-methoxy-1,2,3,4-tetrahydroisoquinoline by reaction with ethylene carbonate and tetrabutylammonium bromide in THF dry and then by reaction with TsCl and pyridine. Tosyl derivative was treated with [$^{18}$F]K-(Kriptofix 2.2.2)F, potassium carbonate and acetonitrile for 4 min a 80° C. After addition of $H_2O$ (2 mL), $^{18}$F radioligand was purified on reverse phase chromatography column with 100 mM $NaH_2PO_4$:EtOH 1:1 (v/v) as mobile phase. The quality control of the product is then carried out on preparative HPLC before use in vivo.

Biological Assays

1) Apparent Permeability Determination ($P_{app}$)

This assay is carried out on colon adenocarcinoma cell line (Caco-2) overexpressing P-gp, a cell model usually employed for the permeability study. In this experiment Apparent Permeability (Papp) is determined both in basolateral/apical direction (Papp-BA) and in apical/basolateral direction (Papp-AB). The BA/AB ratio allow to discriminate if a ligand is transported by P-gp (BA/AB ratio between 18 and 20), or not (BA/AB ratio between 1 and 2). For BA/AB ratio between 2 and 18 compounds can be classified as modulators (see Polli, J. V et al., 2001, *J. Pharmacol. Exp. Ther.* 299, 620-628).

2) ATP Cell Depletion Determination on MDCK Cell Lines Overexpressing MDR Proteins.

This assay is useful to detect the ATP cell level in cells after treatment with MDR ligands. Therefore, if ligand is transported by P-gp, it will be ATP cell depletion whereas if there is not ATP depletion, the ligand is not transported by P-gp. This assay is a bioluminescent assay that use the enzymatic reaction of conversion of luciferin to oxiluciferin mediated by luciferase (see Kangas, L. et al., 1984; *Med. Biol.*, 62, 338-343).

3) Inhibition of the Transport of Calceina-AM and of Rhodamine-123 on MDCK Cell Lines Overexpressing MDR Proteins.

In this assay the inhibition of the transport of a BCRP fluorescent substrate, Rhodamina-123, or of a P-gp or MRP1 profluorescent substrate, Calcein-AM, is determined.

The fluorescent signal due to the accumulation of Rhodamine-123 in cells is inversely correlated to the efflux pump activity.

Calcein-AM, entering the cell membrane is idolized by citosolic esterase to fluorescent calcein (that is not a P-gp substrate) leading to a fluorescent signal. Therefore, the inhibition of the efflux pump will be directly correlated to the fluorescent signal due to the cell accumulation of Calcein-AM (see Feng, B., et al., 2008; *Drug Metab. Dispos.* 36, 268-275).

From the combination of these three biological assays it is possible to classify the tested ligands as substrates, modulators or inhibitors.

Results Obtained in the Biological Assays

The results obtained in the above-described assays with some representative compounds are reported in the Table 1. The results highlighted that the molecules of the invention are able to interfere with P-gp activity as inhibitors or as modulators thereof, but they show poor or no activity towards MRP1.

More in details the oxazole derivative (R=OH) was a potent P-gp inhibitor ($EC_{50}$=2.8 μM) and was inactive towards MRP1 whereas other oxazole derivatives (R=H and R=F) were P-gp inhibitors ($EC_{50}$=2.7 μM and 5.2 μM, respectively) moderately active towards MRP1 ($EC_{50}$>30 μM). The other compounds tested have shown modulating activity towards P-gp and were inactive towards MRP1.

MRP1 pump is another ABC transport displaying high homology with P-gp, but these transporters differ from cell localization; P-gp is localized at apical level, whereas MRP1 at basolateral compartment.

TABLE 1

| compound | $EC_{50}$ P-gp (μM) | $EC_{50}$ MRP1 (μM) | Papp BA/AB |
|---|---|---|---|
| $R_2$ = H, $R_1$ = Br, X = O | 1.8 | >100 | 3.2 |
| $R_2$ = H, $R_1$ = OH, X = O | 2.80 | >100 | 1.6 |
| $R_2$ = H, $R_1$ = $OCH_3$, X = O | 0.60 | 14.7 | 3.8 |
| $R_2$ = H, $R_1$ = F, X = O | 5.20 | 31.8 | 0.80 |
| $R_2$ = H, $R_1$ = H, X = O | 2.70 | 33.2 | 0.40 |
| $R_2$ = H, $R_1$ = Br, X = S | 3.70 | >100 | 6.0 |
| $R_2$ = H, $R_1$ = $OCH_3$, X = S | 1.00 | >100 | 6.0 |

REFERENCES

1. Vogelgesang, S. et al. 2002, *Pharmacogenetics*, 12, 535-541

2. Rapposelli et al., 2009, *Curr. Top. Med. Chem.*, 9, 209-217
3. Kuhnke, D. et al., 2007, *Brain pathol.*, 17, 347-353
4. Bart, J. et al., 2003, *Neuroimage*, 20, 1775-1782
5. Liow, J. S. et al., 2009, *J. Med. Chem.*, 49, 1328-1335
6. Dörner, B. et al. 2009, *J. Med. Chem*, 52, 6073-6082
7. Luurtsema, G. et al., 2009, *Nucl. Med. Biol.*, 36, 6073-6082;
8. Bankstahl, J. P. et al., 2008, *J. Nucl. Med. Chem.*, 49, 1328-1335
9. Kannan, P. et al., 2009, *Clin. Pharmacol. Ther.*, 86, 368-377;
10. Kannan, P. et al., 2010, *ACS Chem. Neurosci.*
11. PCT Int. Appl. (2000) WO0071101 Methods and compounds for inhibiting amyloid deposits.

The invention claimed is:
1. A compound having formula I:

Formula I

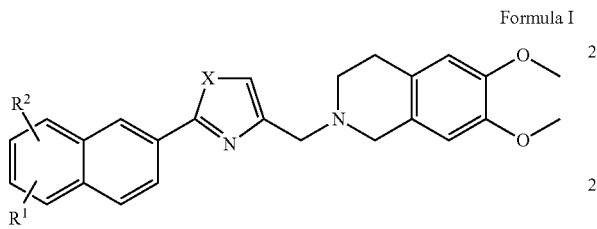

wherein
X is oxygen or sulfur;
$R^1$ is OH, $OCH_3$, or Br; and
$R^2$ is H.

2. A compound according to claim 1, wherein the compound is isotopically radiolabeled.

3. The compound according to claim 1, wherein the compound is labeled with an isotope selected from the group consisting of $^3H$, $^{11}C$, $^{14}C$, $^{13}N$, $^{15}O$.

4. A diagnostic imaging composition comprising as imaging agent a compound according to the claim 2 and a carrier.

5. The diagnostic imaging composition according to claim 4 for use in vivo diagnosis of a neurodegenerative disease involving P-glycoprotein.

6. The diagnostic imaging composition according to claim 5 wherein the neurodegenerative disease is the Alzheimer's or Parkinson's disease.

7. The diagnostic imaging composition according to claim 4 in the form of an injectable solution wherein the imaging agent concentration is from 4 mg/ml to 7.5 mg/ml.

8. A pharmaceutical composition comprising a compound according to claim 1 and a pharmacologically acceptable excipient and/or diluent.

9. A pharmaceutical kit formed by a first element containing a compound according to claim 1 and a second element containing radionuclide suitable for imaging.

10. A method of preparing a compound according to claim 1, comprising transforming a compound of formula II into the compound of formula I via intermediate compound III according to the following scheme with 1,3-dichloroacetone (C) and 6,7-dimethoxy-1,2,3,4-tetrahydroisoquinoline (D):

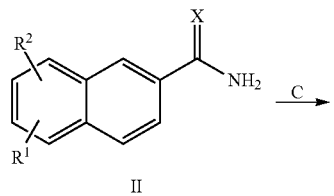

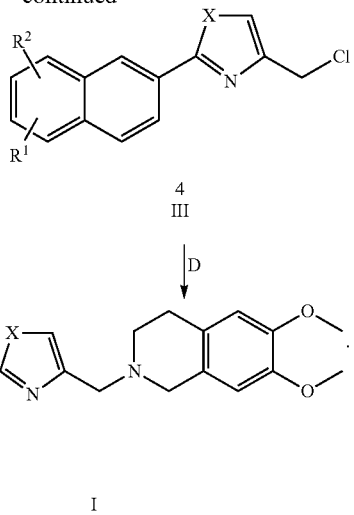

wherein the compound of formula I is isolated and optionally purified and wherein: X is oxygen or sulfur; $R^1$ is OH, $OCH_3$, or Br; and $R^2$ is H.

11. The method according to claim 10, further comprising the step of reacting with a radioisotope.

12. A method for treatment of a neurodegenerative disease that can be treated by modulating P-glycoprotein activity, comprising administering to a patient requiring such treatment an effective amount of a compound according to claim 1.

13. The method according to claim 12, wherein the neurodegenerative disease is Alzheimer's disease or Parkinson's disease.

14. A method for in vivo diagnosis of a neurodegenerative disease involving P-glycoprotein, comprising:
(a) administering to a patient an effective amount of a isotopically radio labelled compound according to claim 2; and
(b) imaging the P-glycoprotein within the patient.

15. The method according to claim 14, wherein the neurodegenerative disease is Alzheimer's disease or Parkinson's disease.

16. The method according to claim 14, wherein the diagnosis is performed by positron emission tomography (PET) or single photon emission computed tomography (SPECT) analysis.

17. The method according to claim 12, wherein for the compound acts as inhibitor or as modulator of P-glycoprotein function in prevention or treatment of a pathology involving P-glycoprotein.

18. A compound according to claim 1, wherein the compound is

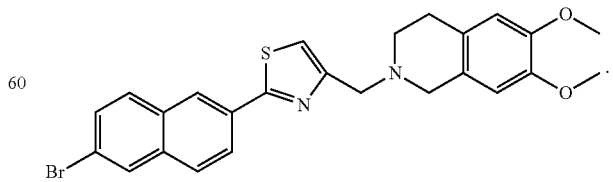

19. A compound according to claim 1, wherein the compound is

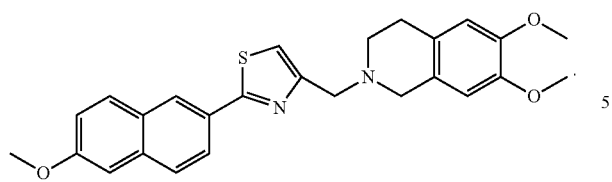
20. A compound according to claim 1, wherein the compound is
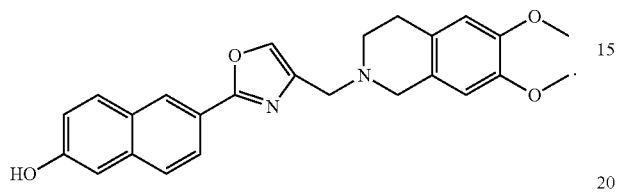
* * * * *